United States Patent [19]

Takayanagi

[11] Patent Number: 4,863,910

[45] Date of Patent: Sep. 5, 1989

[54] COMPLEXES OF AZO COMPOUNDS AND/OR THEIR SALTS AND AN ANTITUMOR AGENT AND A METHOD FOR REDUCING THE GROWTH OF TUMORS

[76] Inventor: Takeo Takayanagi, 41 Ellsworth Ave., Yonkers, N.Y. 10705

[21] Appl. No.: 876,834

[22] Filed: May 20, 1986

[51] Int. Cl.[4] .................. C07C 107/00; C07C 107/04; C07C 107/06; C07C 107/08
[52] U.S. Cl. .................................... 514/150; 534/643; 534/787; 534/827; 534/829; 534/832; 534/646; 534/728; 534/653; 534/716; 564/210; 564/428; 564/443; 560/163
[58] Field of Search ............... 534/643, 827, 832, 797, 534/829, 650, 646, 728, 716; 514/150

[56] References Cited

U.S. PATENT DOCUMENTS

| | | | |
|---|---|---|---|
| 2,243,617 | 5/1941 | Bonhote et al. | 534/827 |
| 3,546,202 | 12/1970 | Bydesinsky et al. | 534/827 X |
| 4,145,299 | 3/1979 | Ford et al. | 534/827 X |

FOREIGN PATENT DOCUMENTS

| | | | |
|---|---|---|---|
| 2703492 | 8/1978 | Fed. Rep. of Germany | 514/150 |
| 55-45607 | 3/1980 | Japan | 514/150 |
| 55-45608 | 3/1980 | Japan | 514/150 |
| 55-145699 | 11/1980 | Japan | 514/150 |
| 56-32472 | 4/1981 | Japan | 514/150 |

Primary Examiner—Floyd D. Higel
Attorney, Agent, or Firm—Bierman and Muserlian

[57] ABSTRACT

A complex of an azo compound of the formula

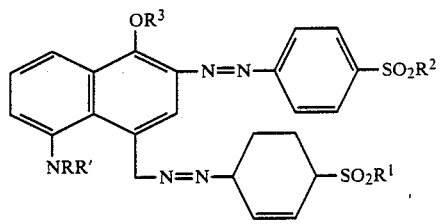

wherein R and R' are selected from the group consisting of hydrogen $-COCR_4{}^3$, $-COCHR_2{}^4$, $SO_2CH_3$ $-CO_2C_2H_5$, $-CH_2CH_2R^4$, $-(CH_2CH_2R^4)_2$, $-CH_2CH_2OH$, $-CONHCH_2CH_2R^4$ and $-CH_2CH_2OCOHN_2$, $R^4$ is selected from the group consisting of chlorine,

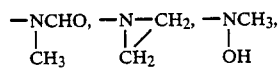

$-NHCO_2CH_2CH_2OH$, $-HNCO_2C_2H_5$, $-NHOH$, $-NHCONHOH$ and $-NHCH_3$; $R^1$ and $R^2$ are individually selected from the group consisting of

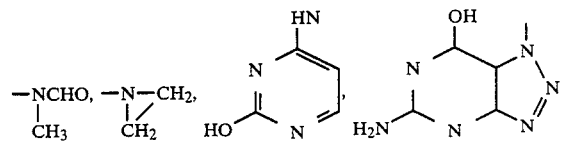

$-NHCH_2CH_2Cl$, $-NHCONHOH$, $-NHCO_2C_2H_5$, 6-mercapropurin, 5-fluoruracil and prenissolin, $R^3$ is selected from the group consisting of hydrogen, $-COCHR_2{}^4$, $-SO_2CH_3$, $-COC_2H_5$, $-CH_2CH_2R_4$ and $-CONH_2$, $R^4$ is the same as defined herein above, or their pharmaceutically acceptable metal salts, and an antitumor agent selected from the group consisting of nitrogen mustard, cyclophosphamid, thyothepa, 6-mercaptopurine, 5-fluoruracil, vinblastine, L-asparaginase and prednisolone and treatment of tumors and living tissue.

16 Claims, No Drawings

COMPLEXES OF AZO COMPOUNDS AND/OR THEIR SALTS AND AN ANTITUMOR AGENT AND A METHOD FOR REDUCING THE GROWTH OF TUMORS

This invention relates to the new azocompounds, their azo complex compounds, together with process for producing the same, and more particularly is concerned with producing pharmaceutical preparation containing the same as effective ingredient.

The new azocompounds are represented by the following general formula I

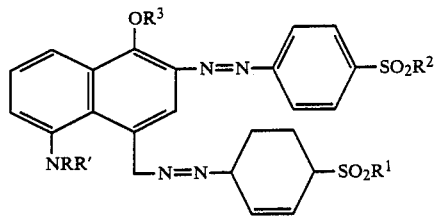

Wherein

R and R' are hydrogen, —COCR$_3^4$—COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$CH$_2$OH, —CONHCH$_2$CH$_2$R$^4$ or —CH$_2$CH$_2$OCONH$_2$ and R$^4$ is Cl or a group of the formula

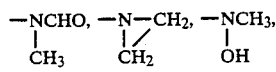

—NHCO$_2$CH$_3$CH$_2$OH  —NHCO$_2$C$_2$H$_5$, —NHOH, —NHCONHOH or NHCH$_3$, whereby R and R' are similar or dismilar.

R$^1$. and R$^2$ are

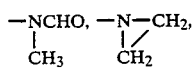

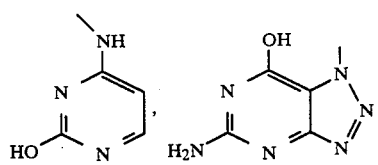

—NHCH$_2$CH$_2$Cl, —NHCONHOH, NHCO$_2$C$_2$H$_5$, 6-mercaptpurinyl, 5-fluorruracilyl, sulfisomidyl or prednisolyl, whereby R$^1$ and R$^2$ are similar or dissimilar.

R$^3$ is hydrogen, —COCHR$_2^4$, —COCR$_3$HU 4, —SO$_2$CH$_3$, —COC$_2$H$_5$ —CH$_2$CH$_2$R$^4$ or —CONH$_2$.

And R$^4$ has the meaning above mentioned, whereby R and R$^3$ are similar or dissimilar.

The new azocompounds form salts especially pharmaceutically acceptable metal salts, and they are employed in the producing of complex-compounds. The azocompound of formula I, its salt especially metal salts can be easily form the the complex-compound with the following selected compounds, for example, antitumor agents:
cyclophosphamide, thiotepa, 6-mercaptopurine, vinblastine, 6-mercaptopurine, 5-fluoruracil, L-asparaginase, nitromine or prednisolone.

antibiotica: chloramphenicol, streptomycin or penicillin.

curative organic dyestuff:
pyoktanin, methylene blue or acriflavin.

organic compounds having therapeutic effect:
abscisinic acid, p-hydroxybenzoic acid, maleic acid, D-glucosaminehydrochloride glucoside.

The compounds of the formula I can be not only coagulated with 1 component above mentioned, but it can be also coagulated with several components at a time, which are similar or various groups of action. The condensation of the compounds having the formula I were carried out smoothly in coherent medium under dropping of selected metal salt solution.

Hereby employed meal salts were selected out of many metals according to the purpose.

The new comprex compounds of this invention have accurate inhibitory properties against the growth of tissue, therefore the complex are available for treatment of malignant tumor or new formation even mycosis etc. Due to their macromolecular constitution, the complexcompounds are well tolerable by the human body and shows no side effect. Furthermore all the complexcompounds are easily soluble in water or in saline solution, consequently it is convenient for clinical use.

Furthermore, it is now substantiated that this invention has the advantage of obtaining many effective substances through adequate variation and combinatin of the substituents and the condensation components.

Finally it has been founded numerous new effective compounds necessary for combination therapy in the treatment of malignant disease.

The compounds of this invention are, as above mentioned nearly non toxic, tasteless or have no side effects, may be per as taken with good tolerance. Therefore they are suitable for preparing pharmaceutical composition which is an object of this invention.

According to this invention the manufacturing of the compounds having following formula III.

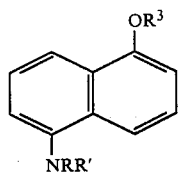

Wherein R,R' and R$^3$ have the meaning above mentioned, were coupled with (a) 2 mole of diazosulfonamide-component having the formula

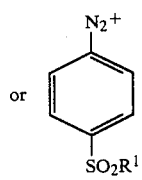

(b) with 1 mole of component IVa, IVb each one after an other

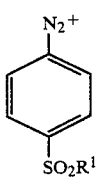

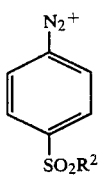

Whereby $R^1$ and $R^2$ are dismimilar and have the meaning above mentioned.

The compounds thus obtained can be employed in the preparation of complex-compounds with 5-Fluoruracil, Cyclophosphamide, 6-Mercaptopurin, P yoktanin, Prednisolon, Methylenblue, Vinblastin, Abcisinic acid, Maleic acid, or L-Asparaginase.

The azocoupling reaction of the compounds of formula III is smoothly effected in the well-known manner upon cooling. Hereby I have founded that the most suitable diazocomponent for this reaction is ultimately aromatic diazonium group having sulfonamide group indicating in formula IV.

The preparation of chemotherapeutic effective azo-complex-compounds are accomplished in a solvent, particularly in ethylene glycol monoethyl ether, which is character eristically coherent and causes condensation and more over dissolves the compounds above mentioned.

The starting compounds of formula III will be prepared in the well-known manner from 5-amino-1-naphthol (II),

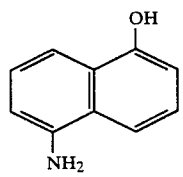

In case of acetylation of 5-amino-1-naphthol 1 mole or 2 equimolecular quantities of acid chloride was reacted at 10° C. When one used equimolecular dichloro or trichloroacetyl chloride, one obtained the compounds having following formula Va and Vb.

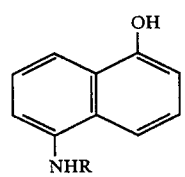

When 2 mole acid chloride applied and by heating 160°–180° C. if needed, catalyst was added then obtained the substance of following formula

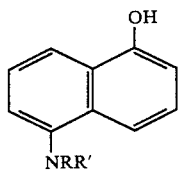

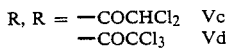

Instead of acid chlorides, similar acid chloride anhydride or isocyanate are employed.

In substitution of 5-amino-1-naphthol(II) with equimolar quantity of 2-chlorethylisocyanat, then obtained the compounds of the following formula

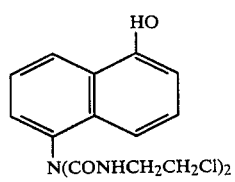

The substitution of 5-amino-1-naphthol (II) with ethylen oxide is carried out in dioxane solution by adding small quantity of water. The obtained compound has the following formula

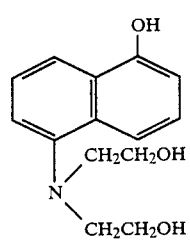

Instead of ethylene oxide can be used hereby another adequate alkylenoxide.

If the amino group of starting substance 5-amino-1-naphthol was already substituted there can be substituted with calcium cyanate in the presence of hydrochloric acid The effected compound is as follows.

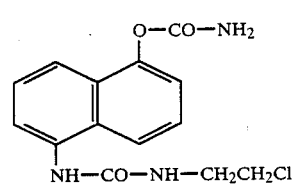

From the compounds of formula III, V-VIII are obtained the compounds of the general formula I by coupling with 2 mole diazo-component of sulfonamide TVa, IVb mentioned above.

The coupled double sulfonamide groups play an important role according to the condensation, especially to the effectiveness, action or reaction of the complex-compounds.

If substitute hydrogen combined with nitrogen by Na, obtained the following formula:

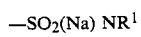

—SO₂(Na) Nr²

If reacted with Magnesium obtained following formula

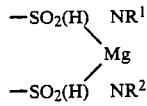

Whereby R¹ and R² are similar or dissimilar.

The following examples will serve to more specifically illustrate preparations according to this invention, as well well as the method of making them.

EXAMPLE 1

1.6 grams of 5-amino-1-naphthol were dissolved in 50 ml pyridine. To the solution there was added drop by drop of trichloroacetylchloride upon cooling at 10° C. or below. The reaction mixture stood over night. Then it was poured into ice and the effected mass was dissolved in a small quantity of ethanol.

The mixture was heated in a pressure bottle for 2 hours at 130 C., adding a slight excess of methylformamides. After the reaction was completed, there was the solution After the reaction was completed there was the solution poured into the diazosulfoethylurethane solution of 2 mole under cooling. Continuously were 5

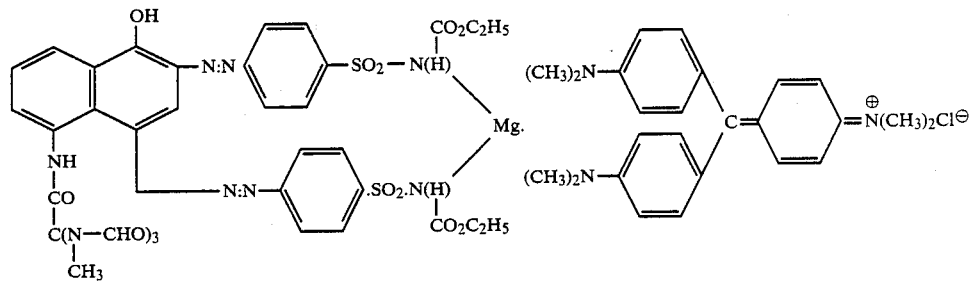

grams of sodium acetate dissolved in water added into the mixture. After standing over night the voluminous precipitate was recovered by filtration. The effected substance is dark almost black colored powder, which was insoluble in water or alcohol and having following formula

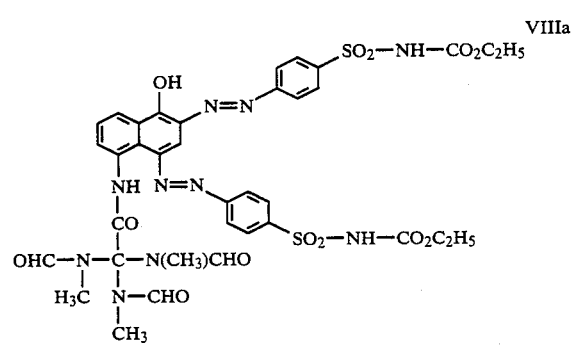

The intermediate products in the stoppered bottle were reacted with ethylenimine and worked up in analogous manner, then obtained dark almost black powder which was insoluble in water and in alcohol having following formula

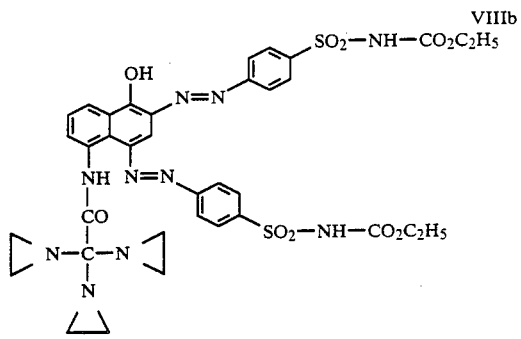

The compound above obtaned of the formula VIIIa and equimolar quantities of methylviolet(pyoktanin) were dissolved in ethylene glycol monomethyl ether. Into this mixture was added dropwise 20% magnesium sulfate soluton until the solution changed to paste finally coagulated, indicating the condensation is completed. Hereupon, the reaction mixture is washed with benzene removing the presented solvent and dried up. The condensation product so obtained is readily soluble in water and in alcohol and it decomposes at over 200 C. under carbonizing having the following cnstitutions formula

EXAMPLE 2

1.6 grams of 5-amino-1-naphthol was reacted in benzene under addition of 5 ml 2-chloroethylisocyanate, whereby obtained the compound of the formula

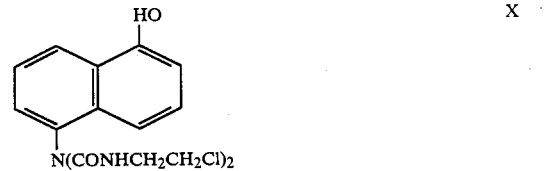

The product is isolated and the substance is mixed with about 6 grams of potassium cyanate. To this mixture is added hydrochloric acid dropwise until the foam forming stops. After standing over night it was treated with water, then resulted precipitate was recovered by filtration and evaporated to dryness. The product obtained above has following formula

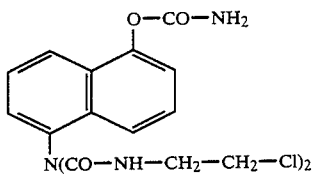

The resulted mass was dissolved in 150 ml ethanol. The solution was added to the solution in the well-known manner prepared 2 mole of diazosulfacytosine solution under cooling and finally was added into this solution 5 grams of sodium acetate dissolved in water. The effected voluminous precipitate was recovered by filtration. The new product has the following formula

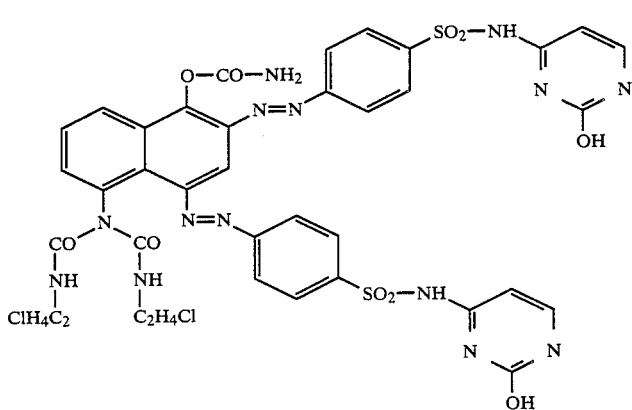

The resulted substance was in adequate quantities of ethylene glycol monomethyl ether dissolved. Into the solution was added equimolecular quantities of pyoktanin. successively was sodium hydroxide solution dropwise added until the solution turns purple colored. At this point in the condensation completed.

The substance will be isolated as a dark powder which is readily soluble in water. The compound is decomposed at 200° C. and has the following constitution formula C.–40° C., there can be obtained the product of following formula

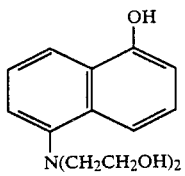

The substance obtained above was in small quantities of ethanol dissolved, and was added upon cooling to the solution of, in the well-knowned manner prepared, 2 mole of diazosulfomethylamine solution upon cooling and finally, 5 grams of sodium acetate dissolved in water were added into the solution. The effected voluminous precipitate was recovered by filtration. The product has the following constitution formula

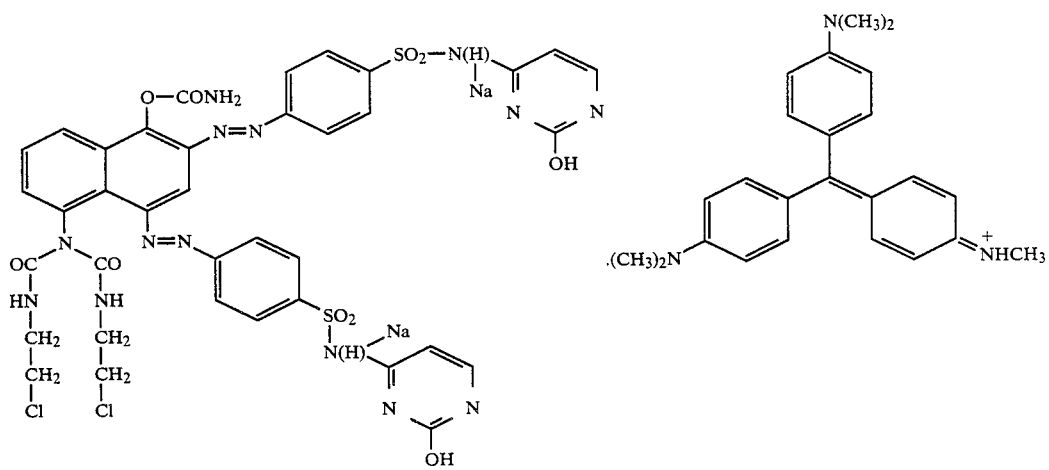

EXAMPLE 3

A mixture of 3 grams of 5-amino-1-naphthol, 20 ml dioxane, 6 ml distilled water and 6 grams of ethylenoxide were heated for two hours in a pressure bottle at 30°

XV

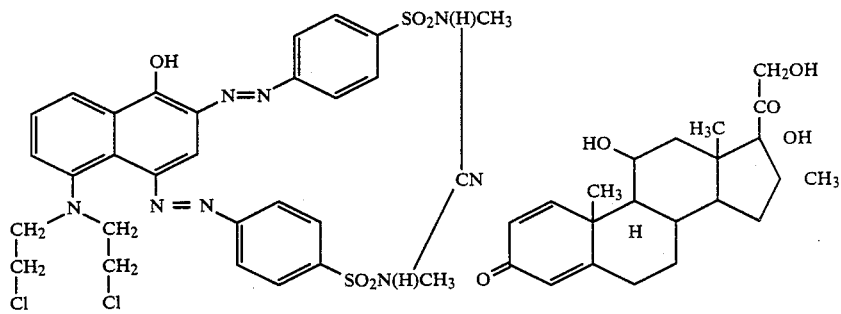

solvent with benene, the resulted compound was dried up.

The product is readily soluble in water and azure colored powder having the following formula

XVII

The resulted substance was dissolved in 50 ml of benzene by adding 2-3 ml of pyridine. Into the reaction mixture were added 10 ml of thionyl chloride drop by drop. The substitution will be completed after 2 hours of heating. The resulted substance has the following formula

XVI

The resulted substance was dissolved in a adequate quantities of ethylene glycol monomethyl ether and to the solution added equimolecular quantities of prednisolone. Hereupon, to the solution was added copper sulfate solution drop by drop until the solution initially formed quickly congeals to a paste which is immediately turns coaglate. After washing and removal of

EXAMPLE 4

1,6 grams of 5-amino-1-naphtol was reacted in benzene with 5 ml of 2-chlorethylisocyanate, whereby obtained the compound of the formula

XVIII

The effected product was isolated and the substance is mixed with 5 grams of potassium cyanate and to this mixture was added hydrochloric acid solution drop by drop. Finally stopped the foaming and standing over night. The reaction mixture was treated with water and isolated the product having the following formula

XIX

The resulted mass was dissolved in small qunatities of ethanol. The solution there was added into the 2 mole quantities of dazosulfisomidine solution upon cooling. Continuously, into the mixture was added 5 grams of sodium acetate dissolved in water.

The effected voluminous precipitate was recovered by filtration. The product has the following constitution formula

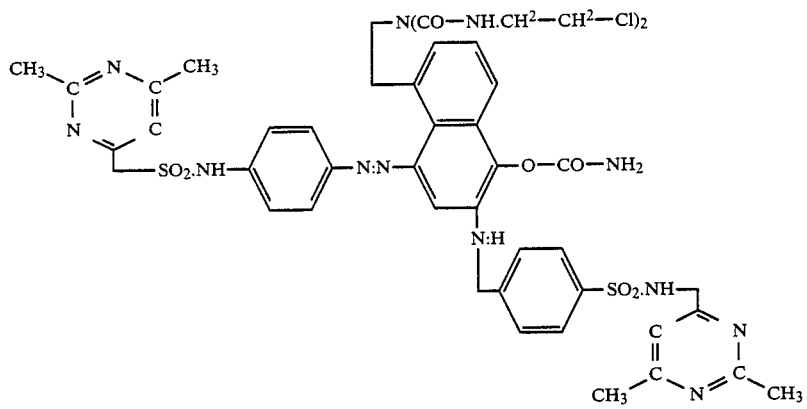

XX

The compounds above mentioned having formula XX and equimolecular quantities of methyl violet, abscisinic acid or prednisolone were dissolved in a adequate quantity of ethylene glycol monomethyl ether.

Hereupon, into the mixture were $MgSO_4$ solution dropping-wise added until the mixture changed to paste and quickly coaglated. At this point the condensation is completed. The condensation product so obtained is easily soluble in water and alcohol and it decmposes at over 200° C. under carbonizing. The constitution formula of the product as follows

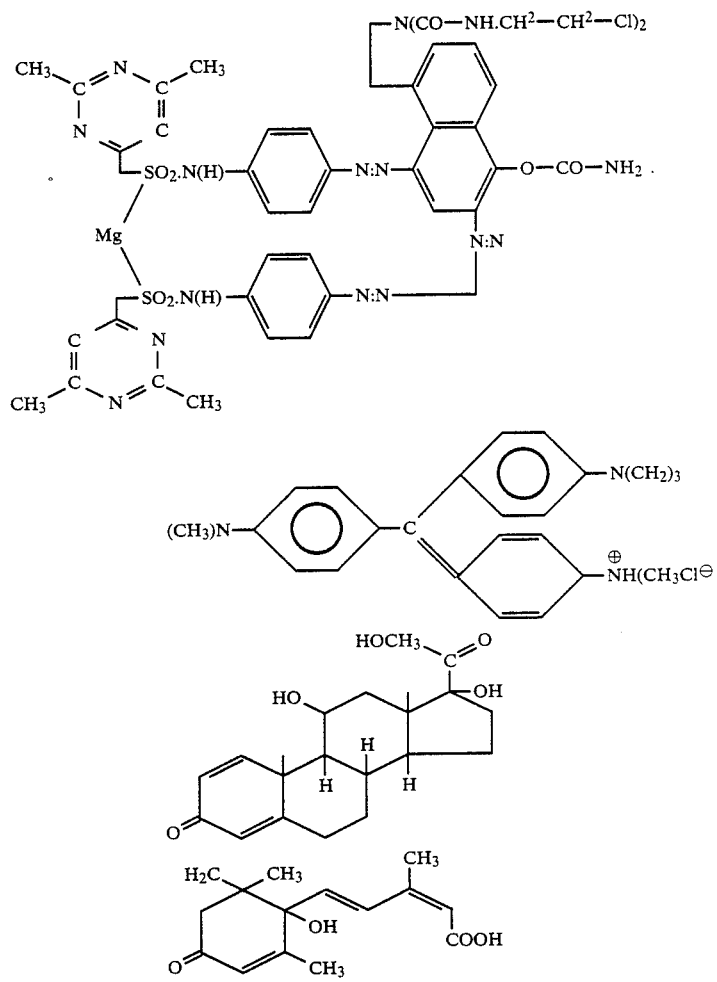

What is claimed is:
1. A complex of an azo compound of the formula

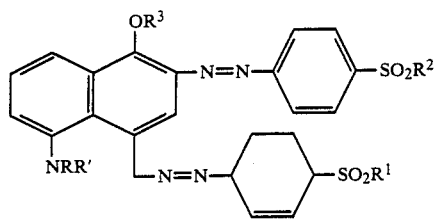

wherein R and R' are selected from the group consisting of hydrogen, —COCR$_3^4$, —COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$CH$_2$OH, —CONHCH$_2$CH$_2$R$^4$ and —CH$_2$CH$_2$OCOHN$_2$, R$^4$ is selected from the group consisting of chlorine,

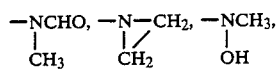

—NHCO$_2$CH$_2$CH$_2$OH, —HNCO$_2$C$_2$H$_5$, —NHOH, —NHCONHOH and —NHCH$_3$; R$^1$ and R$^2$ are individually selected from the group consisting of

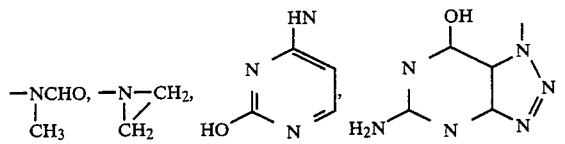

—NHCH$_2$CH$_2$Cl, —NHCONHOH, —NHCO$_2$C$_2$H$_5$, 6-mercapropurin, 5-fluoruracil and prenissolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$, R$^4$ is the same as defined hereinabove, or their pharmaceutically acceptable metal salts, and an antitumor agent selected from the group consisting of nitrogen mustard, cyclophosphamid, thyothepa, 6-mercaptopurine, 5-fluoruracil, vinblastine, L-asparaginase and prednisolone.

2. A complex of an azo compound of the formula

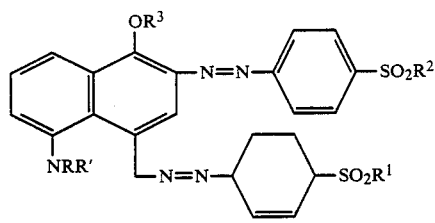

wherein R and R' are selected from the group consisting of hydrogen, —COCR$_3^4$, —COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$CH$_2$OH, —CONHCH$_2$CH$_2$R$^4$ and —CH$_2$CH$_2$OCOHN$_2$, R$^4$ is selected from the group consisting of chlorine,

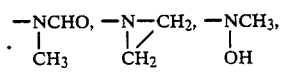

—NHCO$_2$CH$_2$CH$_2$OH, —HNCO$_2$C$_2$H$_5$, —NHOH, —NHCONHOH and —NHCH$_3$; R$^1$ and R$^2$ are individually selected from the group consisting of

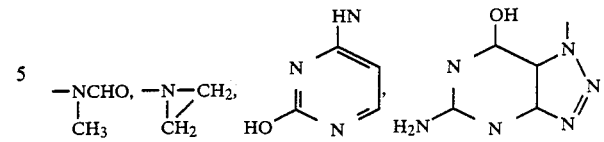

—NHCH$_2$CH$_2$Cl, —NHCONHOH, —NHCO$_2$C$_2$H$_5$, 6-mercapropurin, 5-fluoruracil and prenissolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$, R$^4$ is the same as defined hereinabove, or their pharmaceutically acceptable metal salts, and an antibiotic selected from the group consisting of chloramphenicol, streptomycia and penicillin.

3. A complex of an azo compound of the formula

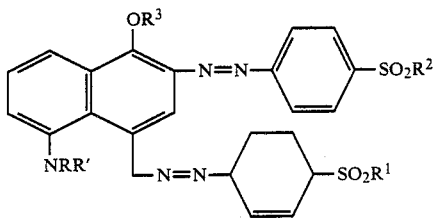

wherein R and R' are selected from the group consisting of hydrogen, —COCR$_3^4$, —COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$CH$_2$OH, —CONHCH$_2$CH$_2$R$^4$ and —CH$_2$CH$_2$OCOHN$_2$, R$^4$ is selected from the group consisting of chlorine,

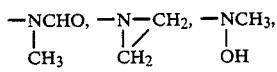

—NHCO$_2$CH$_2$CH$_2$OH, —HNCO$_2$C$_2$H$_5$, —NHOH, —NHCONHOH and —NHCH$_3$; R$^1$ and R$^2$ are individually selected from the group consisting of

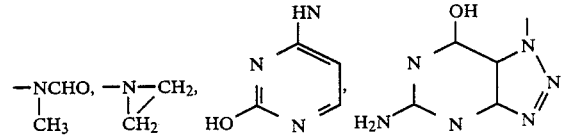

—NHCH$_2$CH$_2$Cl, —NHCONHOH, —NHCO$_2$C$_2$H$_5$, 6-mercapropurin, 5-fluoruracil and prenissolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$, R$^4$ is the same as defined hereinabove, or their salts pharmaceutically acceptable metal, and a curative organic compound selected from the group consisting of pyoktanin (methylviolet), methylene blue and acriflavine.

4. A complex of an azo compound of the formula

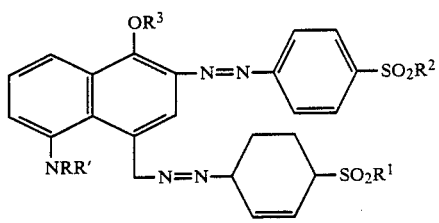

wherein R and R' are selected from the group consisting of hydrogen, —COCR$_3^4$, —COCHR$_2^4$, —SO$_2$CH$_3$, —CO$_2$C$_2$H$_5$, —CH$_2$CH$_2$R$^4$, —(CH$_2$C$_2$R$^4$)$_2$, —CH$_2$C-H$_2$OH, —CONHCH$_2$CH$_2$R$^4$ and —CH$_2$CH$_2$OCOHN$_2$, R$^4$ is selected from the group consisting of chlorine,

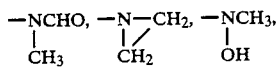

—NHCO$_2$CH$_2$CH$_2$OH, —HNCO$_2$C$_2$H$_5$, —NHOH, —NHCONHOH and —NHCH$_3$; R$^1$ and R$^2$ are individually selected from the group consisting of

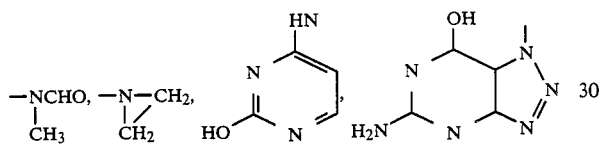

—NHCH$_2$CH$_2$Cl, —NHCONHOH, —NHCO$_2$C$_2$H$_5$, 6-mercapropurin, 5-fluoruracil and prenisolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$, R$^4$ is the same as defined hereinabove, or their salts pharmaceutically acceptable metal, and an organic compound selected from the group consisting of abscisinic acid, p-hydroxybenzoic acid, D-glucosamine and glucoside.

5. A complex of an azo compound of the formula

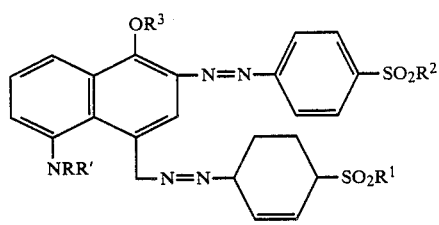

wherein R and R' are selected from the group consisting of hydrogen, —COCR$_3^4$, —COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$C-H$_2$OH, —CONHCH$_2$CH$_2$R$^4$ and —CH$_2$CH$_2$OCOHN$_2$, R$^4$ is selected from the group consisting of Cl,

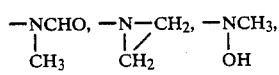

—NHCO$_2$CH$_2$CH$_2$OH, —HNCO$_2$C$_2$H$_5$, —NHOH, —NHCONHOH and —NHCH$_3$; R$^1$ and R$^2$ are individually selected from the group consisting of

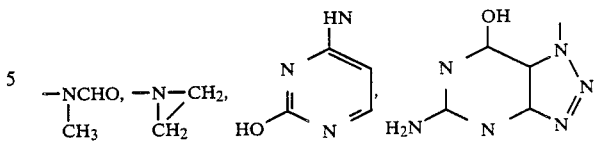

—NHCH$_2$CH$_2$Cl, —NHCONHOH, —NHCO$_2$C$_2$H$_5$, 6-mercapropurin, 5-fluoruracil and prenisolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$ and R$^4$ is the same as defined hereinabove, or their salts pharmaceutically acceptable metal, and an antitumor agent selected from the group consisting of nitrogen mustard, cyclophosphamid, thyothepa, 6-mercaptopurine, 5-fluoruracil, vinblastine, L-asparaginase and prednisolone.

6. A complex of an azo compound of the formula

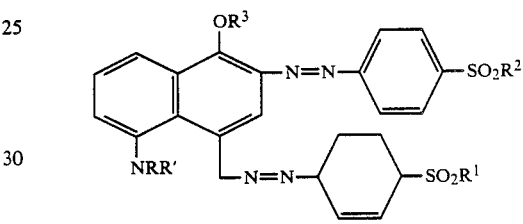

wherein R and R' are selected from the group consisting of hydrogen, —COCR$_3^4$, —COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$C-H$_2$OH, —CONHCH$_2$CH$_2$R$^4$ and —CH$_2$CH$_2$OCOHN$_2$, R$^4$ is selected from the group consisting of Cl,

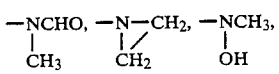

—NHCO$_2$CH$_2$CH$_2$OH, —HNCO$_2$C$_2$H$_5$, —NHOH, —NHCONHOH and —NHCH$_3$; R$^1$ and R$^2$ are individually selected from the group consisting of

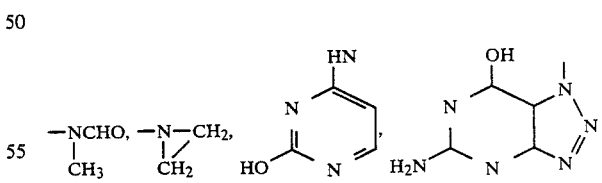

—NHCH$_2$CH$_2$Cl, —NHCONHOH, —NHCO$_2$C$_2$H$_5$, 6-mercapropurin, 5-fluoruracil and prenisolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$ and R$^4$ is the same as defined hereinabove, or their pharmaceutically acceptable metal salts, and an antibiotic selected from the group consisting of chloramphenicol, streptomycia and penicillin.

7. A complex of an azo compound of the formula

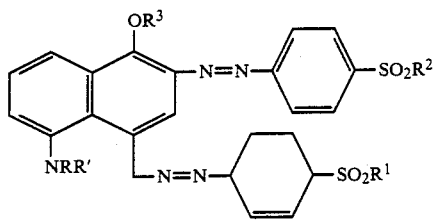

wherein R and R' are selected from the group consisting of hydrogen, —COCR$_3^4$, —COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$CH$_2$OH, —CONHCH$_2$CH$_2$R$^4$ and —CH$_2$CH$_2$OCOHN$_2$, R$^4$ is selected from the group consisting of Cl,

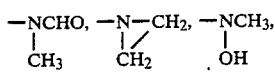

—NHCO$_2$CH$_2$CH$_2$OH, —HNCO$_2$C$_2$H$_5$, —NHOH, —NHCONHOH and —NHCH$_3$, R$^1$ and R$^2$ are individually selected from the group consisting of

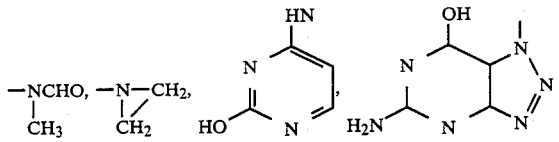

—NHCH$_2$CH$_2$Cl, —NHCONHOH, —NHCO$_2$C$_2$H$_5$, 6-mercapropurin, 5-fluoruracil and prenissolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$ and R$^4$ is the same as defined hereinabove, or their pharmaceutically acceptable metal salts, and a curative organic compound selected from the group consisting of pyoktanin (methylviolet), methylene blue and acriflavine.

8. A complex of an azo compound of the formula

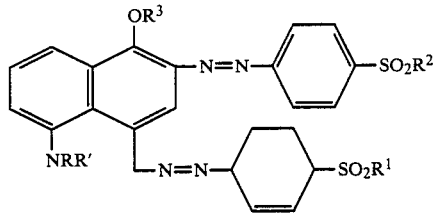

wherein R and R' are selected from the group consisting of hydrogen, —COCR$_3^4$, —COCHR$_2^4$, —SO$_2$CH$_3$, —CO$_2$C$_2$H$_5$, —CH$_2$CH$_2$R$^4$, —(CH$_2$CH$_2$R$^4$)$_2$, —CH$_2$CH$_2$OH, —CONHCH$_2$CH$_2$R$^4$ and —CH$_2$CH$_2$OCOHN$_2$, R$^4$ is selected from the group consisting of Cl,

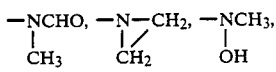

—NHCO$_2$CH$_2$CH$_2$OH, —HNCO$_2$C$_2$H$_5$, —NHOH, —NHCONHOH and —NHCH$_3$; R$^1$ and R$^2$ are individually selected from the group consisting of

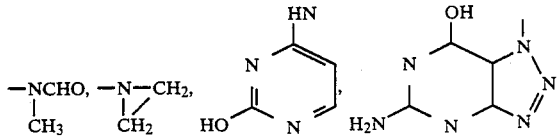

—NHCH$_2$CH$_2$Cl, —NHCONHOH, —NHCO$_2$C$_2$H$_5$, 6-mercapropurin, 5-fluoruracil and prenissolin, R$^3$ is selected from the group consisting of hydrogen, —COCHR$_2^4$, —SO$_2$CH$_3$, —COC$_2$H$_5$, —CH$_2$CH$_2$R$_4$ and —CONH$_2$ and R$^4$ is the same as defined hereinabove, or their pharmaceutically acceptable metal salts, and an organic compound selected from the group consisting of abscisinic acid, p-hydroxybenzoic acid, D-glucosamine and glucoside.

9. A method of reducing the growth of tumors in living tissue comprising the treatment thereof with an effective amount of the complex of claim 1.

10. A method of reducing the growth of tumors in living tissue comprising the treatment thereof with an effective amount of the complex of claim 2.

11. A method of reducing the growth of tumors in living tissue comprising the treatment thereof with an effective amount of the complex of claim 3.

12. A method of reducing the growth of tumors in living tissue comprisign the treatment thereof with an effective amount of the complex of claim 4.

13. A method of reducing the growth of tumors in living tissue comprising the treatment thereof with an effective amount of the complex of claim 5.

14. A method of reducing the growth of tumors in living tissue comprising the treatment thereof with an effective amount of the complex of claim 6.

15. A method of reducing the growth of tumors in living tissue comprising the treatment thereof with an effective amount of the complex of claim 7.

16. A method of reducing the growth of tumors in living tissue comprising the treatment thereof with an effective amount of the complex of claim 8.

* * * * *